United States Patent [19]
Gupta et al.

[11] Patent Number: 5,955,659
[45] Date of Patent: Sep. 21, 1999

[54] ELECTROSTATICALLY-ACTUATED STRUCTURES FOR FLUID PROPERTY MEASUREMENTS AND RELATED METHODS

[75] Inventors: Raj K. Gupta, San Francisco, Calif.; Stephen D. Senturia, Brookline, Mass.

[73] Assignee: Massachusetts Institute of Technology, Cambridge, Mass.

[21] Appl. No.: 09/005,919

[22] Filed: Jan. 13, 1998

[51] Int. Cl.[6] .............................. G01F 1/38; H01L 29/84; G01N 27/00; G01N 11/00
[52] U.S. Cl. .................... 73/54.01; 73/861.47; 73/24.01; 73/778; 361/281; 361/283.4; 422/88; 340/632
[58] Field of Search ................................ 73/54.01, 53.01, 73/23.31, 23.2, 24.01, 23.29, 24.06, 30.04, 31.05, 31.03, 19.03, 778, 780, 599, 861.47; 422/88; 37/92; 340/632; 361/281, 290, 283.4, 283.2

[56] References Cited

U.S. PATENT DOCUMENTS

| | | | |
|---|---|---|---|
| 2,536,025 | 1/1951 | Blackburn | 177/351 |
| 4,361,026 | 11/1982 | Muller et al. | 73/23 |
| 4,674,319 | 6/1987 | Muller et al. | 73/23 |
| 4,686,847 | 8/1987 | Besocke | 73/23 |
| 4,706,100 | 11/1987 | Tufte | 357/16 |
| 4,872,335 | 10/1989 | Tsuroka et al. | 73/30 |
| 4,926,682 | 5/1990 | Holm-Kennedy et al. | 73/54 |
| 5,131,265 | 7/1992 | Tobin et al. | 73/54.23 |
| 5,189,914 | 3/1993 | White et al. | 73/599 |
| 5,199,298 | 4/1993 | Ng et al. | 73/54.01 |
| 5,377,524 | 1/1995 | Wise et al. | 73/4 R |
| 5,417,235 | 5/1995 | Wise et al. | 137/1 |
| 5,445,008 | 8/1995 | Wachter et al. | 73/24.06 |
| 5,453,628 | 9/1995 | Hartsell et al. | 257/76 |
| 5,550,516 | 8/1996 | Burns et al. | 331/65 |
| 5,682,145 | 10/1997 | Sweetman et al. | 340/632 |
| 5,719,324 | 2/1998 | Thundat et al. | 73/24.01 |

FOREIGN PATENT DOCUMENTS

| | | |
|---|---|---|
| 62-145780 | 6/1987 | Japan . |
| 62-147781 | 7/1987 | Japan . |
| 3-63538 | 3/1991 | Japan . |

OTHER PUBLICATIONS

M. Andrews et al., A Comparison Of Squeeze–Film Theory With Measurements On A Microstructure, Sensors and Actuators A, 36 (1993), pp. 79–87.

M. Andrews et al., A resonant pressure sensor based on a squeezed film of gas, Sensors and Actuators A, 36, pp. 219–226 (1993).

M. Andrews et al., A Wide Range Pressure Sensor Using the Squeeze Film Effect, The 7th International Conference on Solid–State Sensors and Actuators, pp. 214–216.

S.T. Cho et al., Secondary Sensitivities and Stabilities Of Ultrasensitive Silicon Pressure Sensors, Center for Integrated Sensors and Circuits, Solid–State Electronics Laboratory, 1990 IEEE, pp. 185–187.

Clark et al., Pressure Sensitivity in Anisotropically Etched Thin–Diaphragm Pressure Sensors, IEEE Transactions on Electron Devices, vol. ED–26, No. 12, Dec. 1979, pp. 1887–1896.

Gupta et al., Pull–In Time Dynamics As A Mesure Of Absolute Pressure, Paper presented at the Tenth IEEE International Workshop on MEMS, Nogoya, JAPAN, Jan. 26–30, 1997, 1997 IEEE.

Gupta, et al., Pull–In Dynamics Of Electrostatiscally–Actuated Beams, Hilton Head 1996 Solid–State Sensor & Actuator Workshop Late News Paper, Jun. 2–6, 1996, pp. 1–2.

Gupta et al., Pull–In Dynamicas Of Electrostatiscally–Actuated Microstructures, SRC TECHCON 1996, Phoenix, Arizona, Sep. 12–14, 1996, pp. 1–4.

Bill Travis, Smart Sensors, EDN, May 9, 1996, A Cahners Publication, vol. 41, No. 10, pp. 57–65.

Milt Leonard, Micromachining Technologies Promise Smarter Sensors, Actuators For A Broad Range Of Applications, Electronic Design, Dec. 4, 1995, vol. 43, No. 25, pp. 35–42.

Cheryl Ajluni, Accelerometers: Not Just For Airbags Anymore, Electronic Design, Jun. 12, 1995, vol. 43, No. 12, pp. 93–106.

*Primary Examiner*—Hezron Williams
*Assistant Examiner*—J. David Wiggins
*Attorney, Agent, or Firm*—Myers Bigel Sibley & Sajovec

[57] ABSTRACT

A fluid property sensor includes a substrate having a first electrode thereon, and a flexible member adjacent the substrate and the first electrode wherein the flexible member includes a second electrode. A signal generator generates a predetermined electrical signal across the first and second electrodes so that an electrostatic force is generated between the first and second electrodes and so that said flexible member deflects a predetermined distance. A measuring circuit measures an interval of time between the generation of the predetermined electrical signal and the deflection of the flexible member to the predetermined distance and determines a property of a fluid adjacent the flexible member based on the interval of time. For example, the sensor can be used to determine a viscosity of the fluid. Alternately, the fluid can be a compressible gas, and the sensor can be used to determine a pressure of the gas. Related methods are also discussed.

78 Claims, 11 Drawing Sheets

ELECTROSTATICALLY-ACTUATED STRUCTURES FOR FLUID PROPERTY MEASUREMENTS AND RELATED METHODS

This invention was made with Government support under Grant Numbers J-FBI-92-196 and J-FBI-95-215 awarded by the United States Department of Justice. The United States Government may have certain rights to this invention.

FIELD OF THE INVENTION

The present invention relates to the field of sensors and more particularly to fluid property sensors and methods.

BACKGROUND OF THE INVENTION

Microelectromechanical sensors have been produced using manufacturing techniques developed in the microelectronics industry. More particularly, fluid property sensors such as pressure sensors have been implemented in Microelectromechanical Systems (MEMS) as discussed, for example, in U.S. Pat. No. 5,453,628 and U.S. Pat. No. 4,706,100. Conventional MEMS pressure sensors measure pressure-induced deflections in diaphragms using capacitance measurements, tunneling current measurements, resonant strain gauge measurements, and piezoresistance measurements. These conventional diaphragm based sensors typically respond to a difference in pressure on two sides of the diaphragm. Accordingly, a known pressure may need to be maintained on one side of the diaphragm.

Other MEMS pressure sensors may measure shifts in mechanical resonance frequencies or thermal conduction to the surrounding gas. Mechanical resonance sensors, however, may have high pressure limits as Q approaches 1. Thermal conduction sensors may have poor resolution at low pressures where conductive heat transfer may be on the order of radiative cooling.

Accordingly, there continues to exist a need in the art for improved microelectromechanical fluid property sensors.

SUMMARY OF THE INVENTION

It is therefore an object of the present invention to provide improved fluid property sensors and related methods.

It is another object of the present invention to provide improved pressure sensors and related methods.

These and other objects are provided according to the present invention by fluid sensors including a substrate having a first electrode thereon and a flexible member adjacent the substrate and the first electrode wherein the flexible member includes a second electrode. A signal generator generates a predetermined electrical signal across the first and second electrodes so that an electrostatic force is generated between the first and second electrodes and so that the flexible member deflects a predetermined distance. In addition, a measuring circuit measures an interval of time between the generation of the predetermined electrical signal and the deflection of the flexible member to the predetermined distance, and the measuring circuit determines a property of a fluid adjacent the flexible member based on the interval of time.

This measured fluid property can be a viscosity of the fluid. More particularly, the fluid can be a gas or a liquid and the viscosity is the resistance that the fluid offers to flow when subjected to a shear stress. Viscosity is also known as flow resistance. Furthermore, the fluid can be a compressible gas, and the measured fluid property can be a pressure of the gas.

The flexible member can be spaced apart from the substrate and the first electrode when in a non-deflected state, and the signal generator can generate the predetermined electrical signal so that an attractive electrostatic force is generated between the first and second electrodes so that the flexible member deflects toward the substrate. Furthermore, the flexible member can deflect toward the substrate so that the first and second electrodes make electrical contact and wherein the interval of time is measured between the generation of the predetermined electrical signal and the electrical contact between the first and second electrodes.

The flexible member can be a polysilicon member, and the flexible member can comprise a beam supported at one end thereon. The flexible member can alternately comprise a beam supported at both ends thereof. The flexible member can also comprise a plate supported by at least one beam, and the plate can be rectangular. Alternately, the flexible member can comprise a diaphragm, and the diaphragm can define a cavity between the diaphragm and the first electrode wherein the cavity is vented. Furthermore, the cavity can be vented through holes in the diaphragm. In addition, the first electrode can include a polysilicon layer on the substrate.

According to the sensors and methods of the present invention, an accurate microelectromechanical fluid property sensor can be provided. The flexible beam approach allows the measurement of absolute pressures without the need to maintain a known pressure. Sensors and methods of the present invention can be used, for example, to provide an indication that a vacuum within a hermetically sealed package for a microelectronic and/or microelectromechanical device has been compromised.

BRIEF DESCRIPTION OF THE DRAWINGS

FIGS. 7a–10a are top views of respective viscosity sensors according to the present invention.

FIGS. 7b–10b are cross sectional views of the respective viscosity sensors of FIGS. 7a–10a.

DETAILED DESCRIPTION

Figure 1:
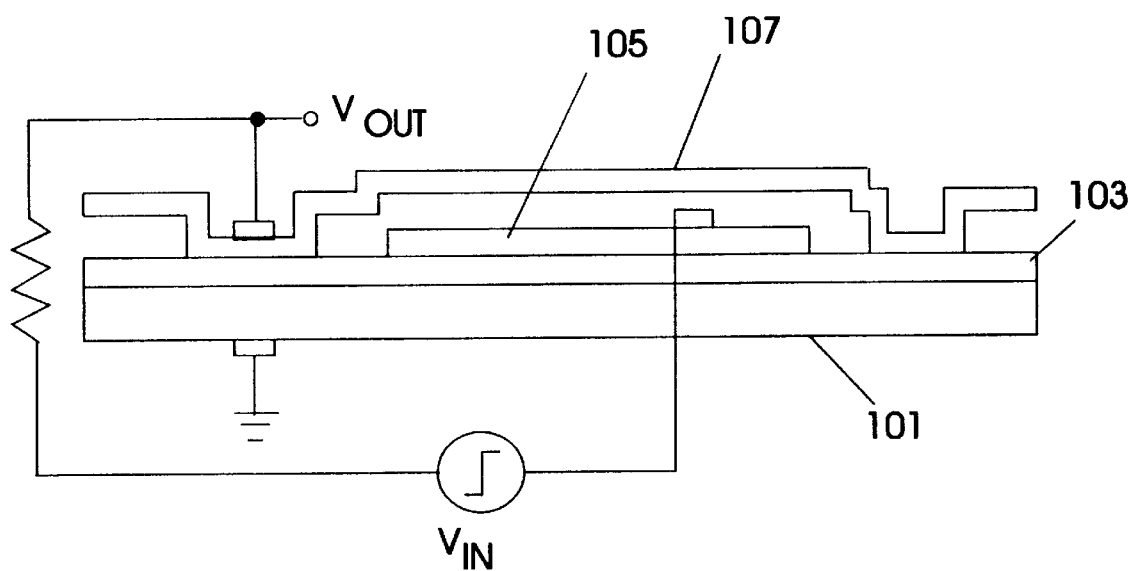
FIG. 1 is a cross sectional view of a viscosity sensor according to the present invention.

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, the thicknesses of layers and regions are exaggerated for clarity. Like numbers refer to like elements throughout. It will also be understood that when a layer is referred to as being "on" another layer or substrate, it can be directly on the other layer or substrate, or intervening layers may also be present.

The squeezed-film damping component of the pull-in time of an electrostatically-actuated micromechanical fixed-fixed beam can be a sensitive, and nearly linear function of ambient air pressure in the range of 0.1 mbar to 1013 mbar (1 atmosphere or 760 Torr). Pull-in time simulations, based on a one-dimensional macromodel using a damping constant proportional to pressure, agree with measured data.

Pull-in type devices can be used to make excellent microelectromechanical systems (MEMS) sensors for broad-range absolute pressure measurements and for in-situ leak monitoring of hermetically sealed packages containing other sensors or IC's. Pull-in sensors are compatible with MEMS fabrication processes that allow out-of-plane electrostatic actuation, including surface micromachining and silicon wafer-bonding. In addition, pull-in sensors do not require a cavity sealed at vacuum or at a reference air pressure.

A deformable parallel-plate structure electrostatically actuated across a narrowing gap may become unstable beyond its static pull-in voltage ($V_{PI}$), a point at which the structure collapses, and makes contact to the opposing electrode, either directly, or on top of a standoff dielectric. Pull-in type devices operated in a mechanically static contact/non-contact mode, are found in microrelays, deformable mirror devices (DMD's), grating light valves (GLV's), and mechanical property test structures.

Figure 2:
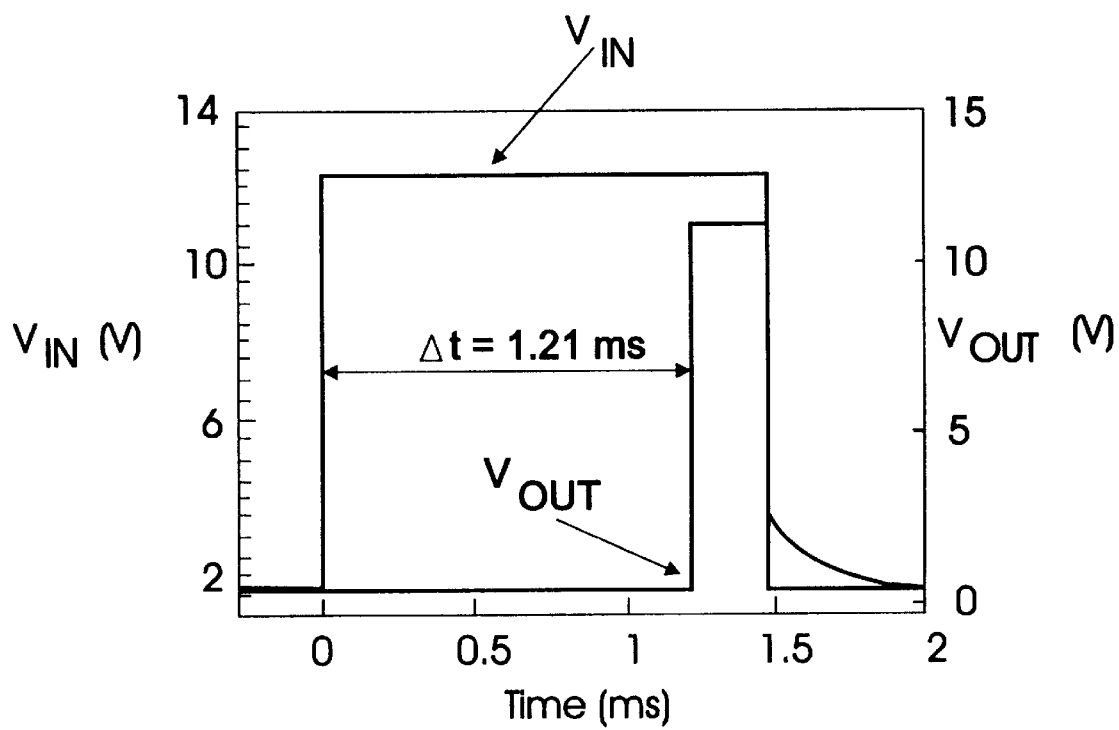
FIG. 2 is a graph illustrating oscilloscope data used to measure the pull-in-time for the viscosity sensor of FIG. 1 wherein the signal generated by the electrical source steps from 1.3 V to 11.8 V. The $V_{in}$ and $V_{out}$ axes are offset and scaled for clarity.

When a pull-in structure is dynamically actuated by an applied step voltage ($V_{APP}$) greater than $V_{PI}$, the pull-in time ($t_{PI}$) is measured as the delay between the step bias application and the structure's contact to the bottom electrode. Measurements performed on a surface-micromachined polysilicon beam fixed at both ends and having a length (L) of 610 $\mu$m, a thickness (t) of 2.2 $\mu$m, a width (w) of 40 $\mu$m, and an undeflected gap (g) of 2.3 $\mu$m. As shown in FIG. 1, the structure includes a silicon substrate 101, a 0.5 $\mu$m thick nitride layer 103, a 0.5 $\mu$m thick polysilicon electrode 105, and a polysilicon beam 107. The beam 107 is electrostatically actuated by a 10 V ($V_{APP}$) zero-to-step bias generated by the voltage source $V_{in}$, which is greater than its static pull-in voltage of 8.76 V. The $t_{PI}$ is determined from switch closure, as shown in FIG. 2.

Figure 3:
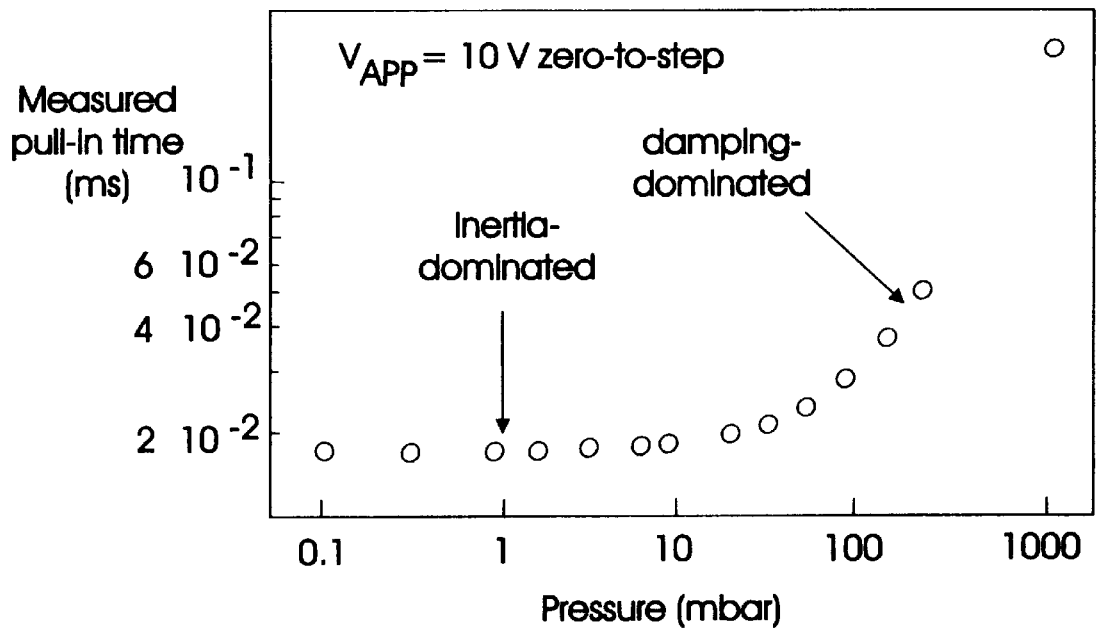
FIG. 3 is a graph illustrating pull-in-times for the viscosity sensor of FIG. 1 as a function of ambient air pressure of a 10 V zero-to-step actuated 610 $\mu$m long beam fixed at both ends wherein the beam is nominally 2 $\mu$m thick and 40 $\mu$m wide and wherein the gap between the beam and the substrate electrode is nominally 2 $\mu$m. The low pressure asymptote is at $t_{PIO}$=18.2 $\mu$s.

Pull-in times for the beam 107 of FIG. 1 are measured as a function of ambient air pressure. FIG. 3 shows that $t_{PI}$ asymptotically approaches a vacuum limit ($t_{PIO}$) of 18.2 $\mu$s, which is determined by the inertia of the system. When $t_{PIO}$ is subtracted from $t_{PI}$, the resulting modified pull-in time $t_{PI}'$, varies almost linearly with pressure over four-orders of magnitude in pressure, as shown in FIG. 4.

Compressible Squeezed-Film Damping (CSQFD) simulations indicate that for $V_{APP}$ between $V_{PI}$ and 5/4 $V_{PI}$, the velocity is constant for more than ¾ of $t_{PI}$. Furthermore, in this region, the beam 107 moves through only a small fraction of the total gap. Hence, the electrostatic force does not change significantly for most of the transient, and the damping force is relatively constant. This scenario is similar to an object moving through a viscous medium at terminal velocity obeying Stokes' law, where the damping force is proportional to velocity. Based on this analogy, the Applicants conclude that a correct first-order damping term for the nonlinear pull-in dynamics can be represented by a standard linear damping force proportional to velocity.

Figure 4:
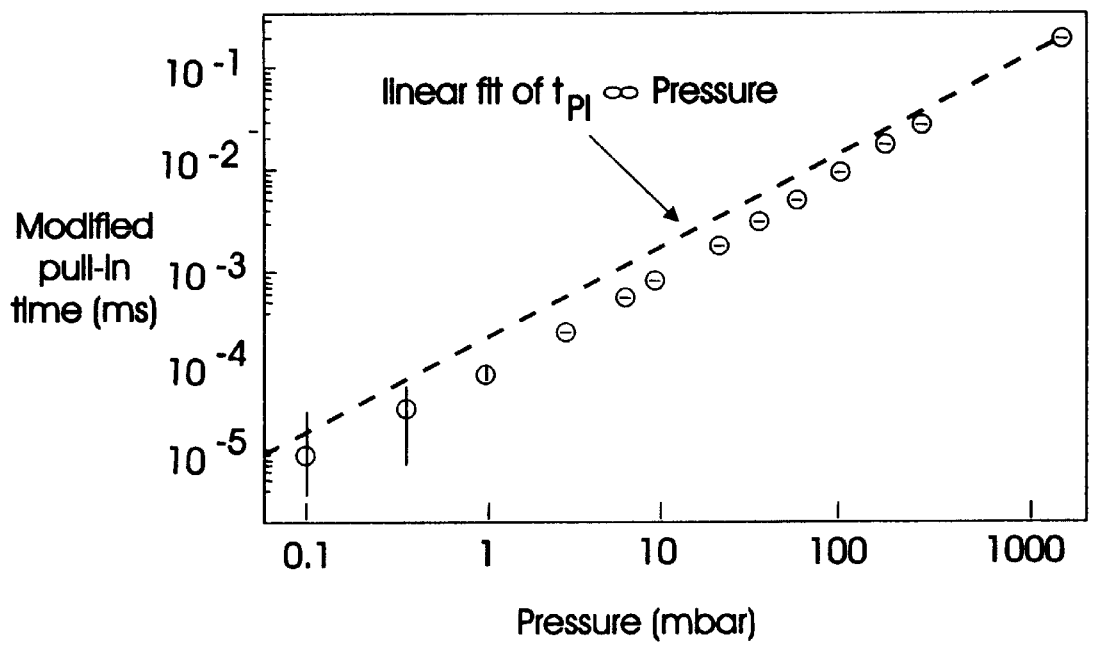
FIG. 4 is a graph illustrating modified pull-in-times ($t_{PI}'$= $t_{PI}$-$t_{PIO}$) as circles. The modified pull-in-times are obtained using the data of FIG. 3 wherein the modified pull-in-times are plotted as a function of ambient air pressure alongside a linear fit (dashed line).

In the limit of linear damping, a one-dimensional (1 D) lumped mass-spring-damper macromodel can be helpful in understanding the experimental results of FIGS. 3 and 4. The 1 D macromodel may also be useful in understanding ways to control the pressure sensitivity of a sensor as will be discussed below.

Figure 5:
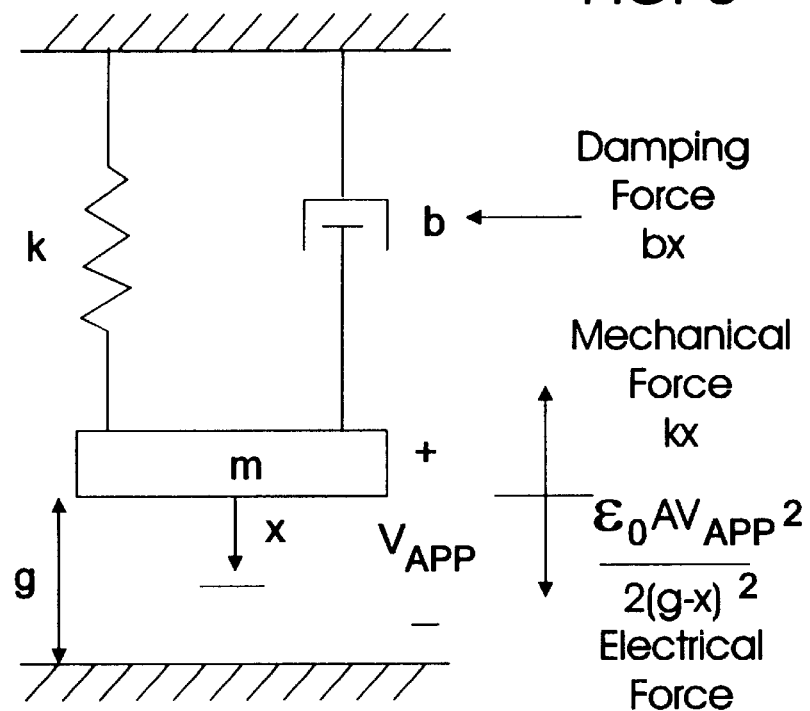
FIG. 5 is a schematic diagram of a 1 D macromodel of a viscosity sensor according to the present invention.

As shown in FIG. 5, the mass m of the 1 D macromodel moves along the x-coordinate, and the electrostatic force is derived from the voltage $V_{APP}$ across the parallel plate capacitance of area A with a gap (g-x). The equation of motion for the 1 D system is given by the following equation:

$$m\ddot{x} + b\dot{x} + kx = \frac{\varepsilon_0 A V_{APP}^2}{2(g-x)^2} \quad \text{Equation (1)}$$

$$\uparrow \qquad \uparrow \qquad \uparrow \qquad \uparrow$$

$$\text{inertia} + \text{damping} + \text{spring} = \text{electrostatic}$$
$$\text{term} \qquad \text{term} \qquad \text{term} \qquad \text{term}$$

The spring constant (k), equal to 4.60 N/m, is determined by matching the 1 D equation for $V_{PI}=(8\ kg^3/27\varepsilon_0 A)^{1/2}$ to the statically measured $V_{PI}$, where A=L×w. The mass (m), equal to 125 ng, is a product of L, w, t, and the polysilicon density p=2330 kg/m$^3$. The damping constant (b) in the 1 D model is determined by matching the experimental pull-in time at 1 atm to the corresponding pull-in time obtained from the numerical integration of equation (1). This yields a b=0.233 g/s at 1 atm, which is then varied proportional to pressure to model $t_{PI}$ data at arbitrary pressures. Numerical integration of equation (1) based on the linear dependence of b with respect to pressure, calculates a $t_{PI}'$ versus pressure relation which is distinguishable from the linear fit in FIG. 4.

At low pressure, the damping term in equation (1) can be neglected, and the system is inertia-dominated. This decreases the pull-in voltage for zero-to-step bias inputs to a new value $V_{DPI}$, which equals $(kg^3/4\rho\varepsilon_0 A)^{1/2}$. Furthermore, an analytic solution (2) can be obtained for $t_{PIO}$, where $T_\alpha$ equals $(m/k)^{1/2}$, and $\alpha$ equals $V_{APP}/V_{DPI}$. With the parameters given above, $t_{PIO}$ is calculated to be 16.8 $\mu$s, which is close to the measured value of 18.2 $\mu$s.

$$t_{PIO} = \int_0^1 T_\alpha \left[ \frac{\alpha^2}{4(1-y)} - \frac{\alpha^2}{4} - y^2 \right]^{-1/2} dy \qquad \text{Equation (2)}$$

At higher pressures, the 1 D system will be damping-dominated, and the spring force will be negligible compared to the damping force. In this limit, $t_{PI}$ will be given by equation (3), where $T_\beta$ equals (b/k), and $\beta$ equals $V_{APP}/V_{PI}$.

$$t_{PI} = T_\beta \int_0^1 \frac{27(1-y)^2}{4\beta^2 - 27y(1-y)^2} dy \qquad \text{Equation (3)}$$

At 1 atm, equation (3) calculates a $t_{PI}$ equal to 233 μs, which is close to the measured value of 235 μs. Note, if the assumption of linear damping is still valid for $V_{APP} \gg V_{PI}$, the inertial term can also be neglected from equation (1), and $t_{PI}$ will become independent of the structure's mechanical properties, as shown in equation (4).

$$t_{PI} \approx \frac{2bg^3}{3\varepsilon_o A V_{APP}^2} \qquad \text{Equation (4)}$$

The assumption of a low Reynold's number regime (R<1) in the CSQFD models is valid in continuum flow for small device geometries and velocities. Reasoning back to previous Stokes' law creeping flow analogies for incompressible fluids in this regime, the damping force ($F_D$) of a normally moving, thin circular plate, of diameter D, can be represented as, $$F_D = C'_D \eta D V \qquad \text{Equation (5)}$$

Where, $C_D'$ is the viscous drag coefficient, which is dependent on the plate shape, η is the air viscosity, and V is the plate velocity. For a circular shape $C_D'$ equals 8. The linear damping force dependence on a plate's lateral dimension can be used to adjust the damping coefficient of a pull-in pressure sensor, and hence, its pull-in time sensitivity.

Figure 6:
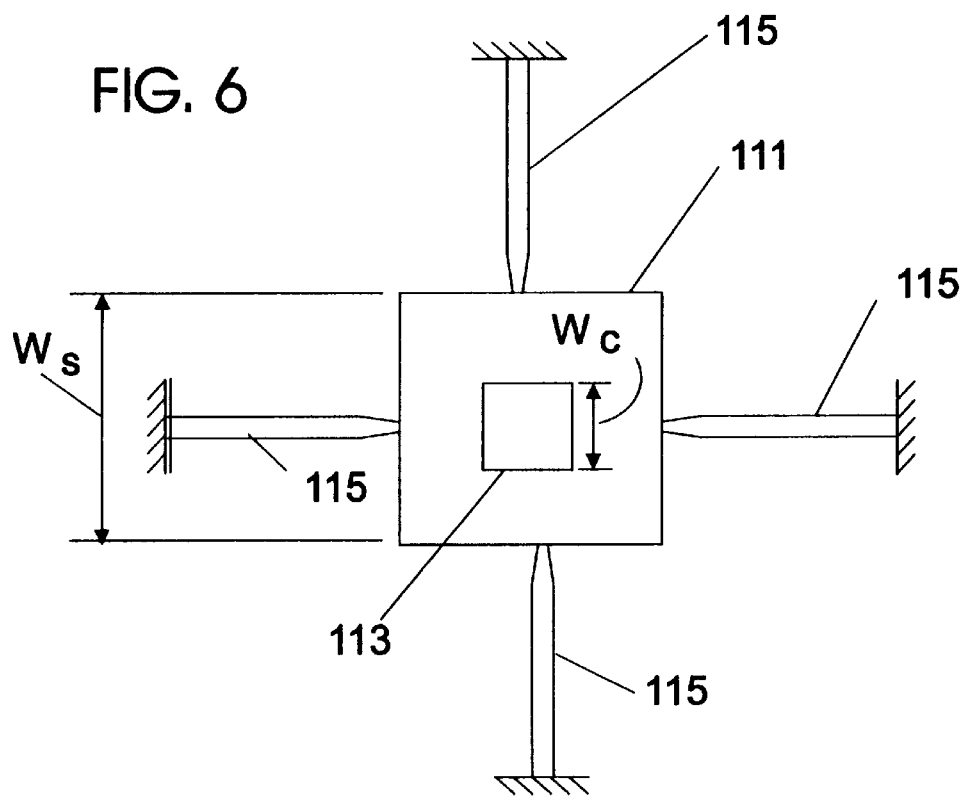
FIG. 6 is a diagram of a pull-in-pressure sensor according to the present invention. The area of the square electrode of width $w_c$ controls the electrostatic force which appears as a tip load on the four supporting cantilevers of the relatively rigid square plate of width $w_s$. The cantilever's length and width, and the square electrode's area determine $V_{PI}$. The moveable plate shape determines the air damping and can be varied to adjust the pressure sensitivity of the sensor.

A diagram of a sensor with a thin uniform thickness is shown in FIG. 6. Analogous to the equation (5) damping dependence on D of the circular plate, the damping dependence of a square plate 111 will be linearly related to its width ($w_s$). Note that $V_{PI}$ will be independent of $w_s$ since the electrostatic load, which is determined by the width ($w_c$) of the underlying square contact 113, will be mainly carried by the mechanical deformation of the narrow cantilever supports 115.

Using equation (3) from the 1 D model, the linear increase in b with $w_s$ predicts that in the damping-dominated regime, $t_{PI}$ will scale proportionally with $w_s$. Similarly, in the inertia-dominated limit, equation (2) predicts that $t_{PIO}$ will scale with $m^{1/2}$, which is linearly dependent on $w_s$. These results indicate that an increase in $w_s$ will produce a vertical shift in the $t_{PI}$ versus pressure relation.

Rough calculations using the 1 D model, where b is proportional to pressure, indicate that the pressure of transition ($P_t$) from the inertia-dominated regime to the damping-dominated regime will occur when $b/(mk)^{1/2} \sim 1$. Based on the 1 D model of the data presented in FIG. 3, this relation correctly estimates that $P_t \approx 100$ mbar.

The above relation can also be used to tailor $P_t$, such that lowering it will reduce the subtraction error in $T_{PI}'$ at low pressures. For the square plate, $b/m^{1/2}$ is independent of $w_s$. However, by reducing the tensile stress in the beams, k (which is independent of $b/m^{1/2}$) decreases and, therefore, decreases $P_t$. Similarly for k of a thin beam, $P_t$ varies inversely with $t^2$ in pure bending, and with t in pure tension.

The pull-in sensor is advantageous in that it can be easily microfabricated alongside other micromachined sensors, and that it can serve as an in-situ monitor for pressure with these sensors and/or integrated circuits. This is important, for example, in measuring leaks in a hermetically sealed micromachined accelerometer package that must maintain critical damping in a narrow range of pressure.

Experience suggests that stiction of the pull-in sensors can be avoided if a low enough operating voltage is chosen. An experiment, using a low frequency (<10 Hz) square-wave excitation on a beam of the type investigated here, was conducted in air at 1 atm over more than a million continuous cycles without showing an observable drift in $t_{PI}$.

Sutherland's expression for the temperature (T) dependence of η, as shown in equation (6), indicates from equation (5) that the damping force of the pull-in sensor will be sensitive to temperature. In equation (6), C is a measure of the attractive molecular forces, and is ~100 K for air at 1 atm. $\eta_0$ is the dynamic viscosity measured at the reference temperature $T_0$.

$$\frac{\eta}{\eta_0} = \left(\frac{T}{T_0}\right)^{1/2} \left(\frac{1 - C/T_0}{1 + C/T}\right) \qquad \text{Equation (6)}$$

While this is not a strong temperature dependence, an in-situ temperature sensor can be used to compensate for temperature variations.

When a microelectromechanical beam's modified pull-in time is plotted versus four-orders of magnitude in pressure, it scales proportionately. The pull-in/response time for the beam can be a few milliseconds or less, and can be simulated with an empirical 1 D macromodel. The 1 D model for damping in low Reynold's number regimes can also be used to predict that the pull-in time can be scaled for pressure sensitivity by adjusting a critical lateral dimension of a pull-in device. The pull-in time for a beam at 1 atm has been found to be stable over a million cycles, and under appropriate biasing conditions, the device can be repeatably operated without stiction.

The models and structures disclosed above are discussed in the reference by inventors of the present invention entitled "Pull-In Time Dynamics As A Measure Of Absolute Pressure," Proceedings of the 10th Annual International Workshop On MEMS, Nagoya, Japan, January 26–30, 1997. The disclosure of this reference is hereby incorporated herein in its entirety by reference.

Variations in the structure of FIG. 1 discussed above are included within the scope of the present invention. For example, the beam can be replaced with a plate or a diaphragm, or the beam can be free at one end thereof. Furthermore, the beam can be formed with materials other than polysilicon. For example, the beam can be formed with a semiconductor material other than polysilicon, a metal such as aluminum, or an insulator such as silicon nitride with a conductive electrode thereon. In addition, the electrode 105 can be provided by the substrate or a portion thereof. Accordingly, the substrate can be defined to include the electrode, for example, as either a portion thereof or as a conductive layer formed thereon, as well as insulating layers therebetween.

Figure 7A:
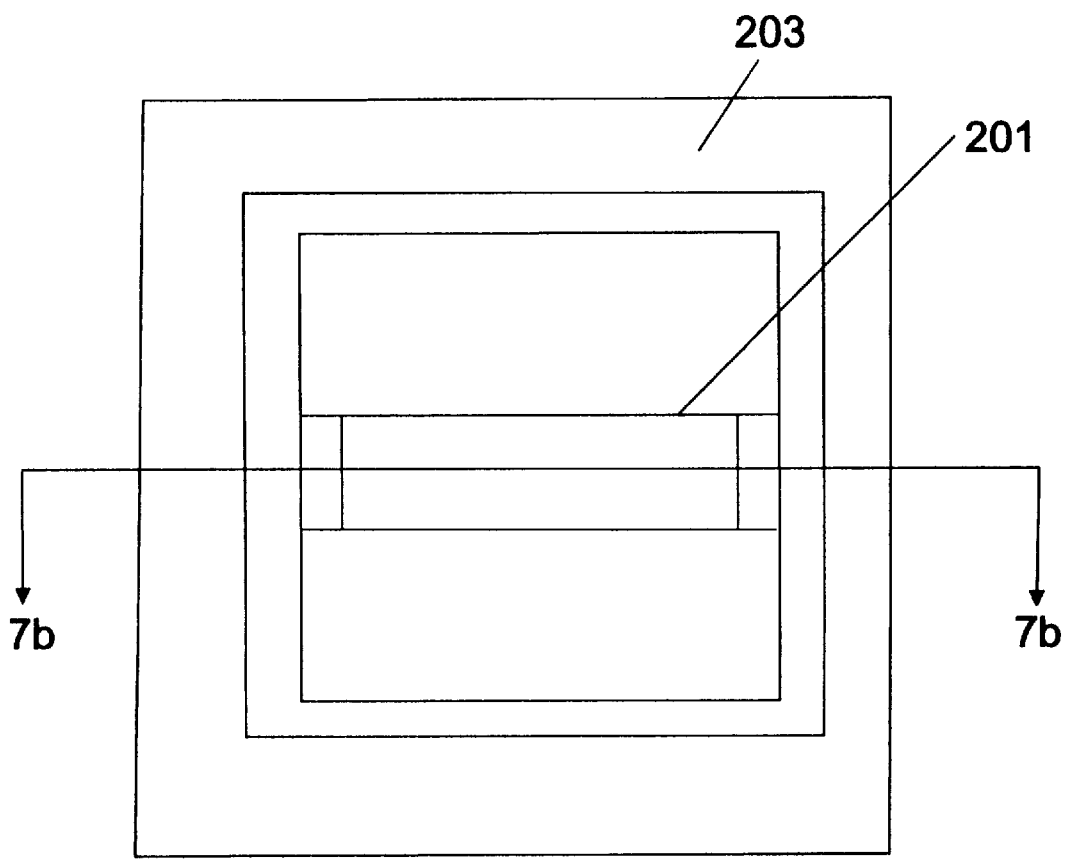
Figure 7B:
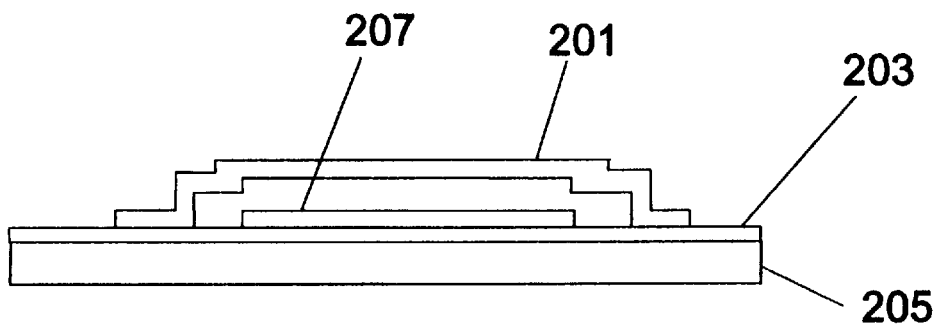

Various pressure sensor structures according to the present invention will now be discussed with reference to FIGS. 7a–b, 8a–b, 9a–b, and 10a–b. As shown in FIGS. 7a and 7b, a pressure sensor according to the present invention can include a flexible beam 201 fixed at both ends thereof. More particularly, the sensor can include an insulating layer 203 such as a nitride layer on a semiconductor substrate 205, and a first electrode 207 on the insulating layer 203. Furthermore, the flexible beam 201 can be a polysilicon beam spaced apart from the first electrode 207. Accordingly, the second electrode on the beam can be provided by doping portions of the beam to increase the conductivity thereof. The first electrode can also be a doped polysilicon layer. In addition, an insulating layer can be provided on either the first electrode of the beam to reduce electrical shorts therebetween. Methods of forming viscosity sensors according to the present invention will be discussed in greater detail with reference to FIGS. 11 a–e.

Figure 8A:
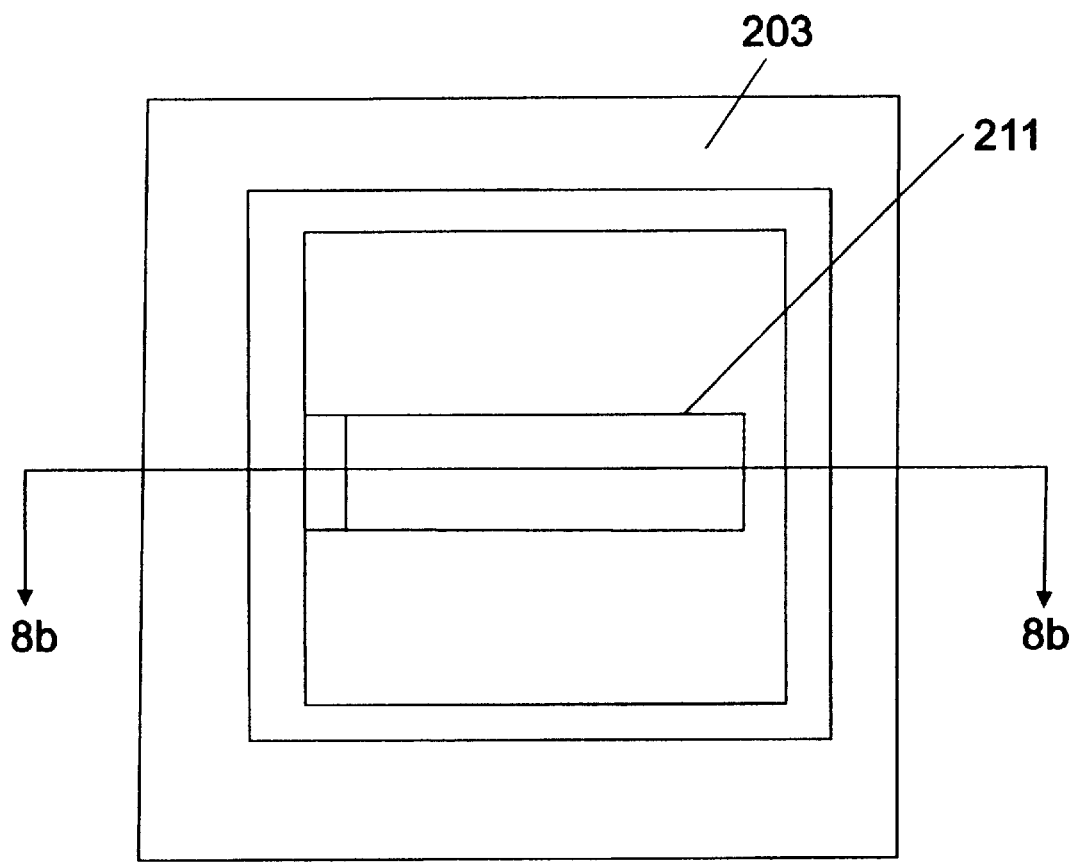
Figure 8B:
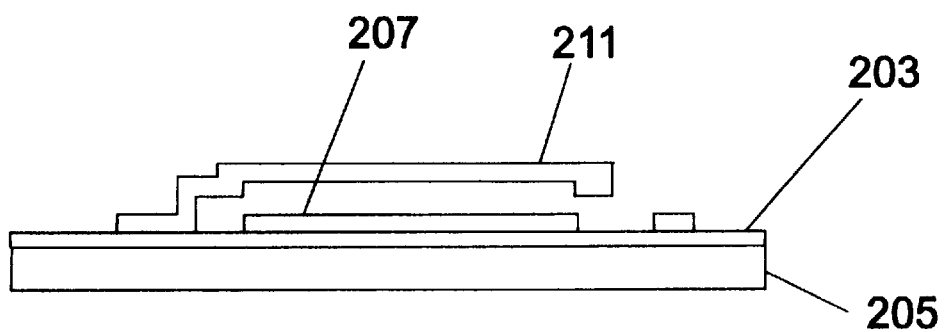
Figure 9A:
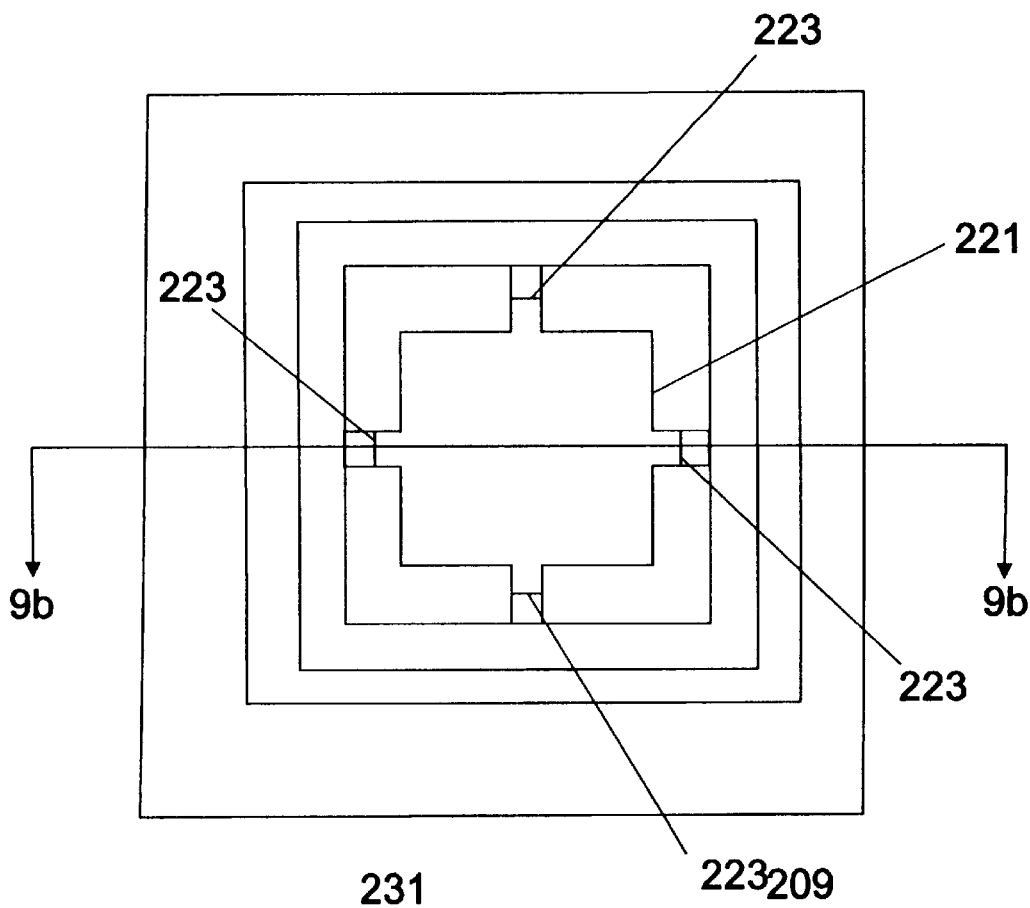
Figure 9B:
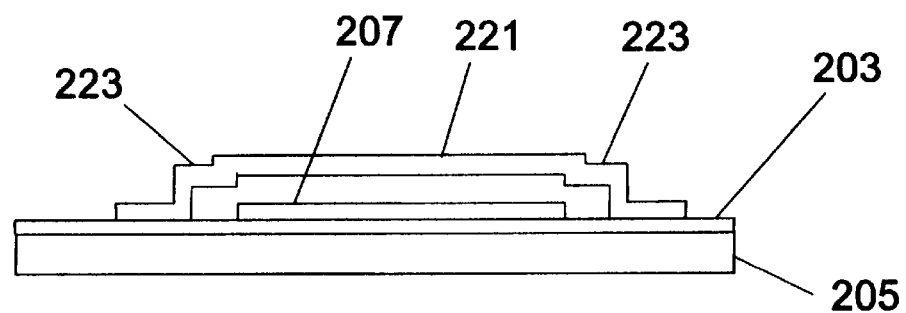

Alternately, the flexible member can be a flexible beam 211 fixed at one end thereof as shown in FIGS. 8a and 8b. The substrate 205, the insulating layer 203, and the first electrode 207 are the same as those discussed above with regard to FIGS. 7a–b. The flexible beam 211, however, is free at one end thereof.

The flexible member can also be a plate 221 suspended by one or more flexible beams 223. The substrate 205, the insulating layer 203, and the first electrode 207 are the same as those discussed above with regard to FIGS. 7a–b and 8a–b. While the plate 221 is illustrated as being rectangular, the plate can have other shapes such as circular, elliptical, or triangular.

Figure 10A:
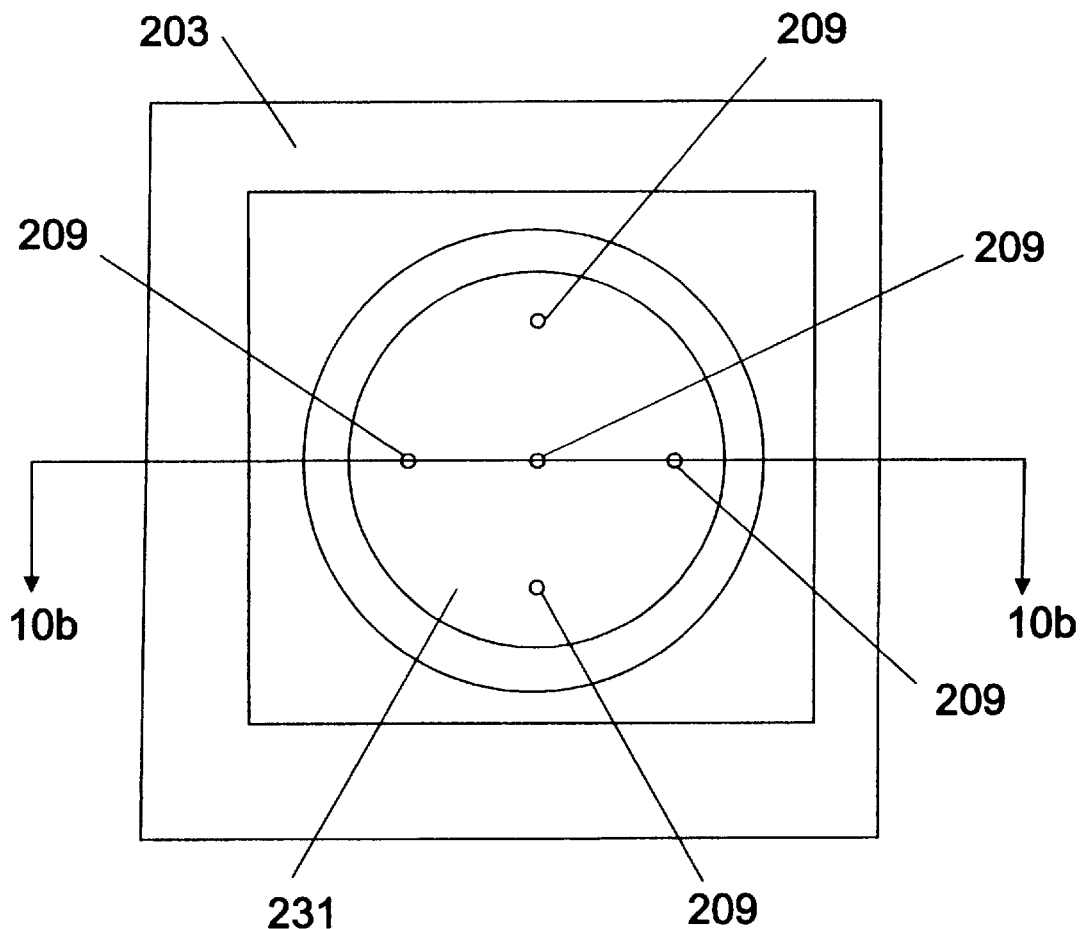
Figure 10B:
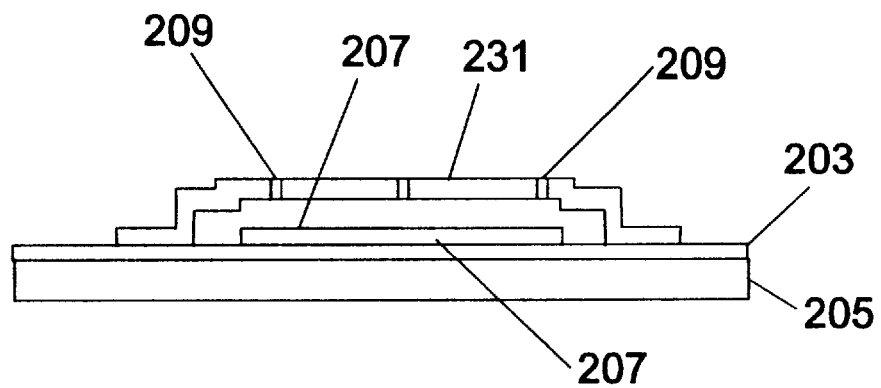

In addition, the flexible member can be a diaphragm 231 as shown in FIGS. 10a–b. The diaphragm 231 defines a cavity between the diaphragm 231 and the first electrode 207, and this cavity is vented. As shown, the cavity can be vented through holes 209 in the diaphragm 231. The substrate 205, the insulating layer 203, and the first electrode 207 are the same as those discussed above with regard to FIGS. 7a–b, 8a–b, and 9a–b. A gas in the cavity between the diaphragm and the first electrode will resist movement of the diaphragm if an electrostatic force is applied between the diaphragm and the first electrode. The speed with which the diaphragm deflects will thus be a function of the pressure of the gas in the cavity, the surface area of the diaphragm, the stiffness of the diaphragm, and the size of the holes therethrough and their location and density. The speed of deflection can thus be used to determine the pressure of the gas. Alternately, the speed with which the diaphragm deflects can be used to determine a viscosity of a fluid adjacent the diaphragm.

Figure 11A:
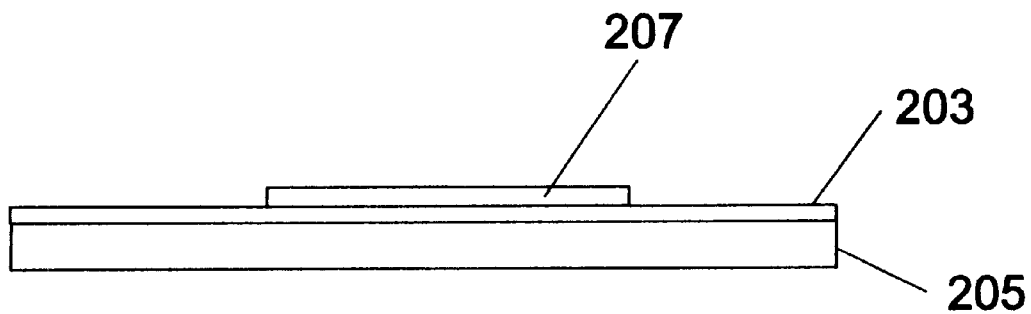
FIGS. 11a–e are cross sectional views illustrating steps of a polysilicon surface micromachining method of forming a viscosity sensor according to the present invention.

Methods of forming the sensor structures discussed above will now be discussed with reference to FIGS. 11a–e. The cross sectional views of FIGS. 11a–e illustrate steps of a method which can be used to form any of the structures of FIGS. 7–10. As shown in FIG. 11a, an insulating layer 203 can be formed on a semiconductor substrate 205, and a first electrode 207 can be formed on the insulating layer 203. In particular, the first electrode can be formed by depositing and patterning a doped polysilicon layer.

Figure 11B:
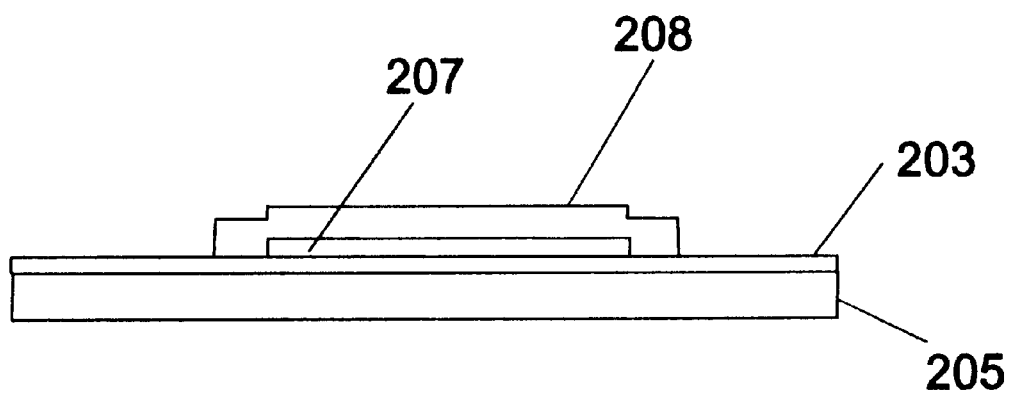
Figure 11C:
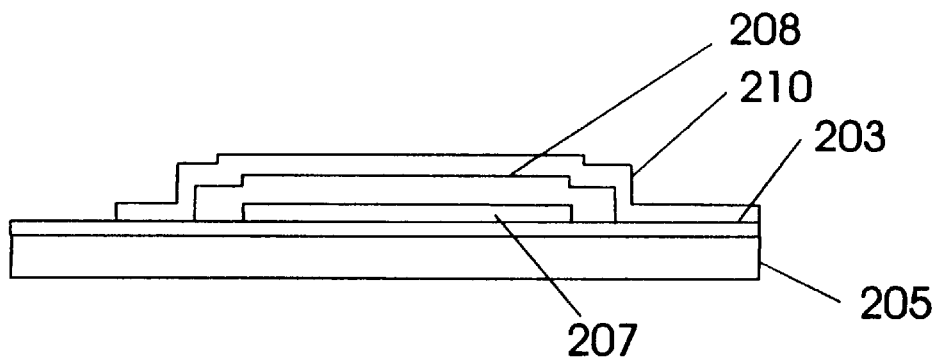

A sacrificial layer 208 is then formed on the first electrode 207 as shown in FIG. 11b. The sacrificial layer 208 can be formed by depositing and patterning an oxide layer to cover the first electrode. A polysilicon layer 210 is then formed on the sacrificial layer 208 and on the exposed portions of the insulating layer 203 as shown in FIG. 11c. The sacrificial layer 208 thus provides a predetermined gap between the first electrode and the polysilicon layer 210 which is used to form the flexible member.

Figure 11D:
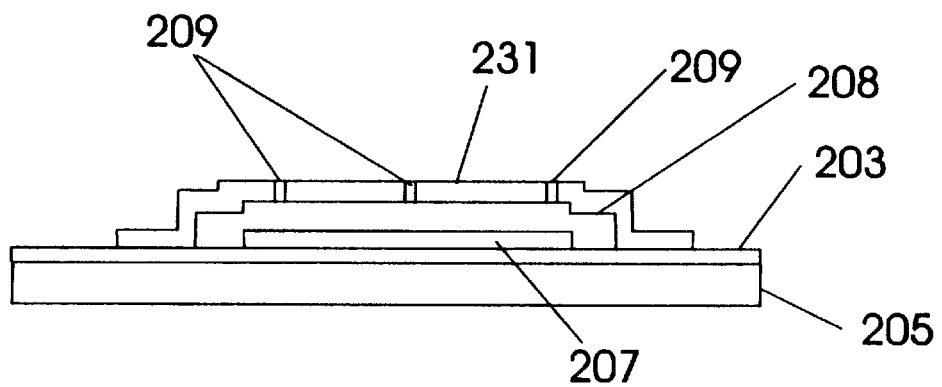
Figure 11E:
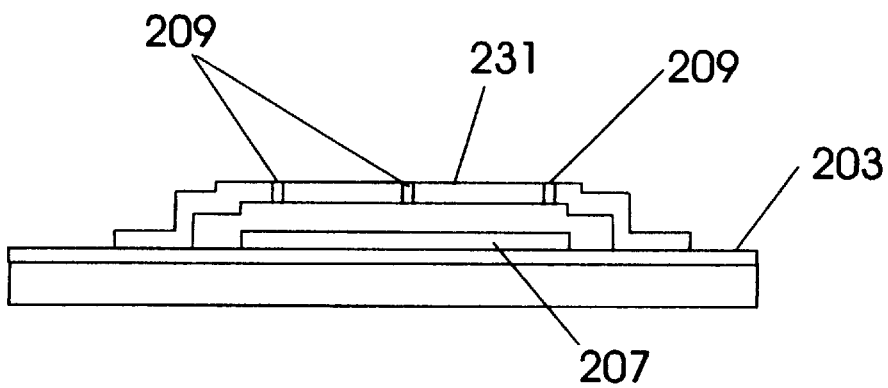

The polysilicon layer 210 is then patterned to provide the desired flexible member as shown in FIG. 11d. The polysilicon layer 210 can be patterned using photolithography and etch steps to form the beam 201 of FIG. 7, the beam 211 of FIG. 8, the plate 221 of FIG. 9, or the diaphragm 231 of FIG. 10. For the purposes of this discussion, the polysilicon layer is patterned to provide the diaphragm of FIG. 10. This patterning step can also be used to simultaneously provide the holes 209 through the diaphragm thus exposing portions of the sacrificial layer 208.

A wet etch can then be used to remove the sacrificial layer 208 thus providing a gap between the diaphragm 231 and the first electrode 207. Portions of the sacrificial layer will also be exposed if the polysilicon layer is patterned into the beams of FIGS. 7 or 8, or the plate of FIG. 9. With these structures, the etch step will thus provide a gap between the flexible member and the first electrode.

Figure 12A:
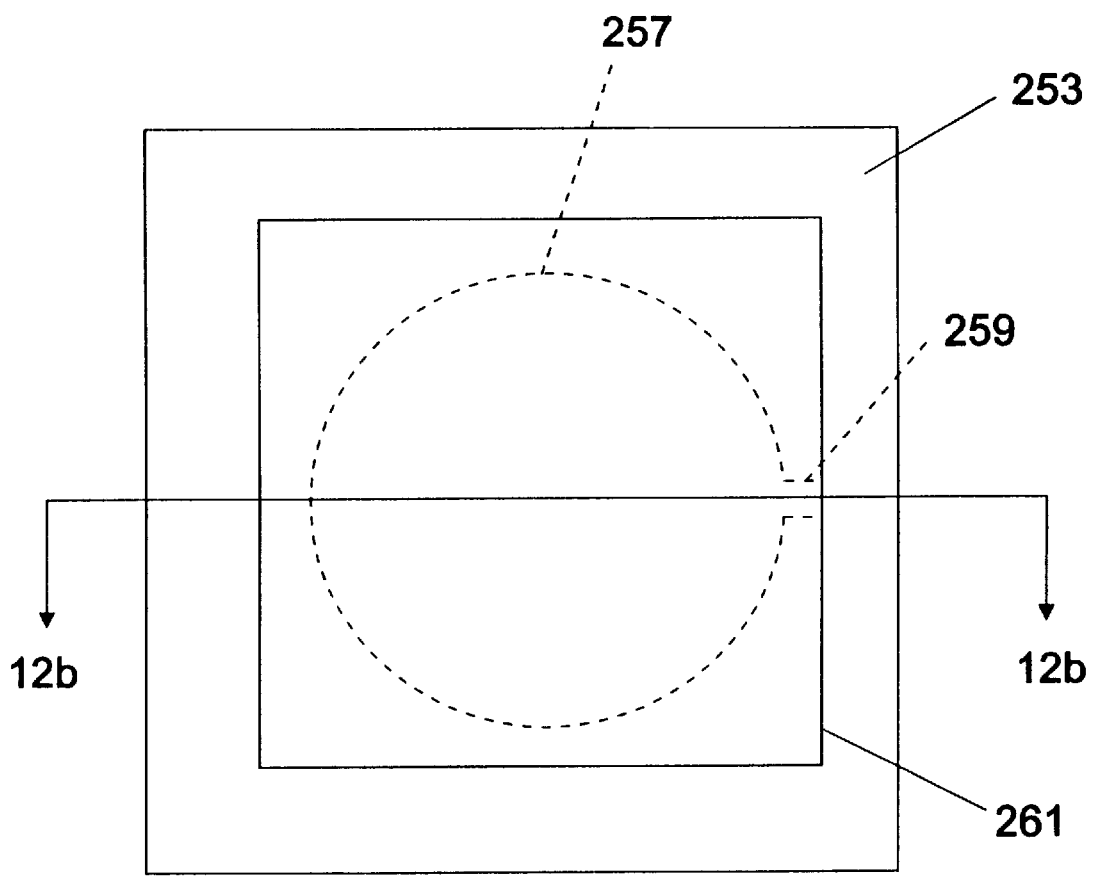
FIGS. 12a–b are respective top and cross sectional views of a viscosity sensor according to the present invention formed using a wafer bonding technique.
Figure 12B:
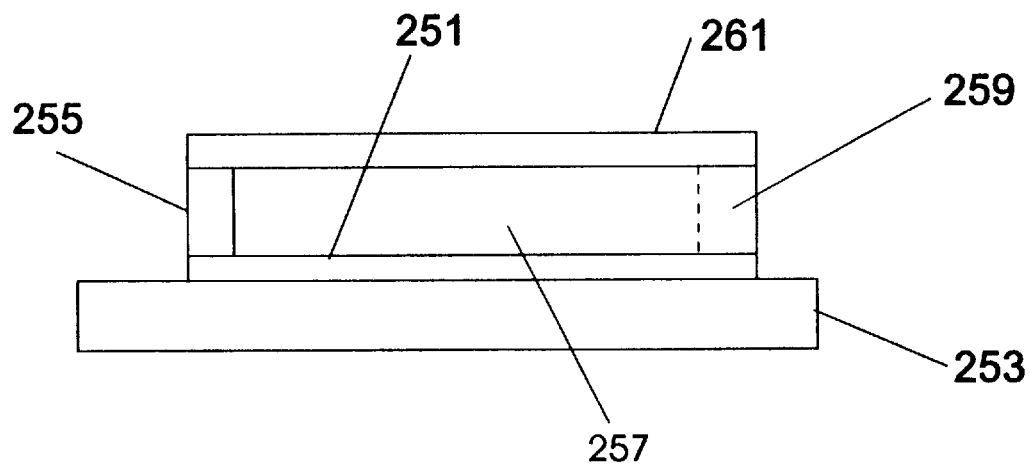

A pressure sensor according to the present invention can alternately be formed using wafer bonding techniques. A sensor formed using wafer bonding is illustrated in FIGS. 12a–b. As shown, the sensor includes a first electrode 251 and a set-off structure 255 on a substrate 253. The set-off structure 255 can be formed by depositing an insulating layer on the substrate and patterning the insulating layer to provide the cavity 257 adjacent the first electrode 251, and the cavity vent 259 through a sidewall of the set-off structure 255. A diaphragm 261 can then be formed by bonding, thinning, and etching a wafer of silicon on top of the set-off structure 255.

Figure 13:
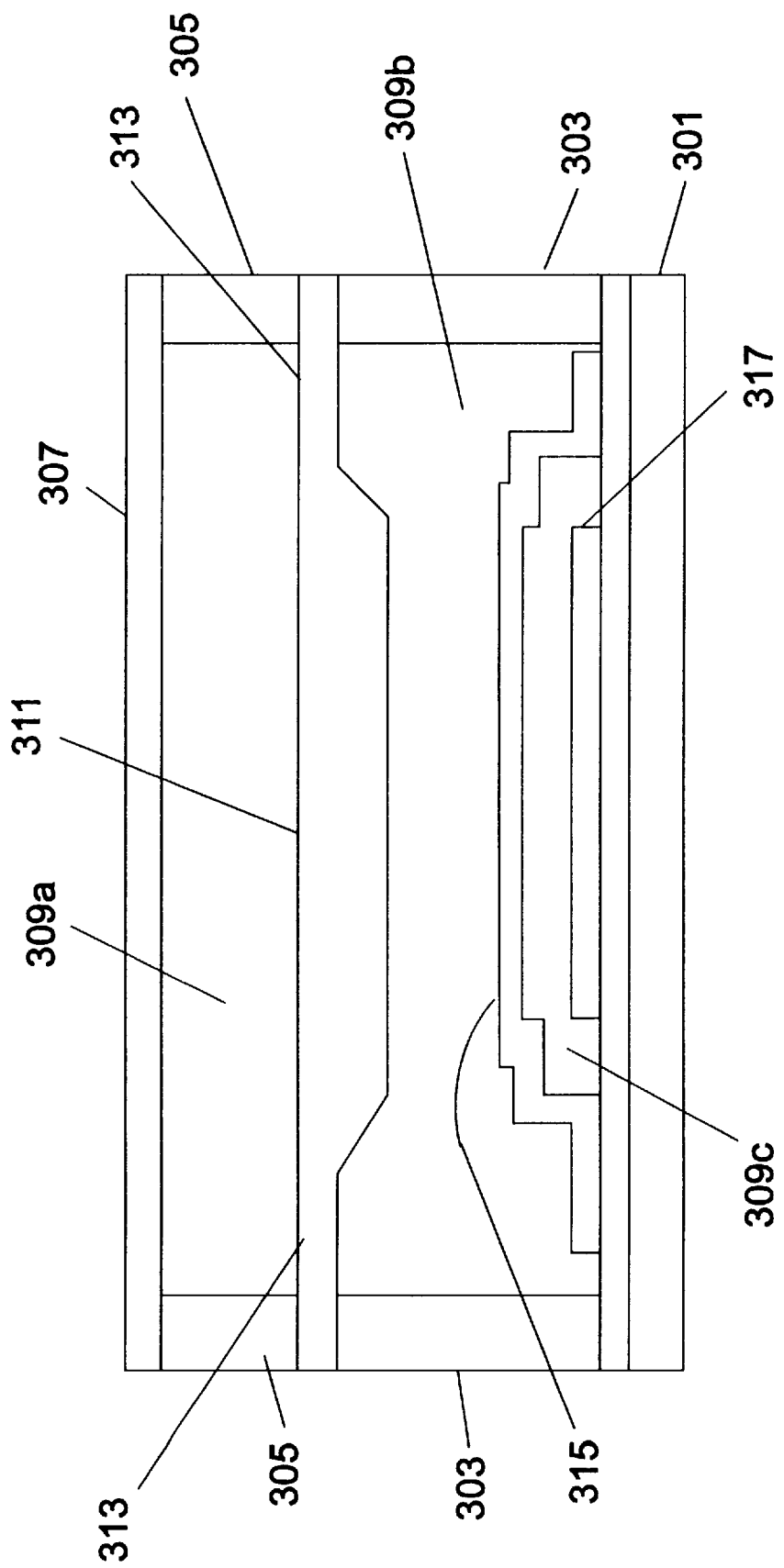
FIG. 13 is a cross-sectional view of a hermetically sealed package including a pressure sensor according to the present invention.

A pressure sensor according to the present invention can be used, for example, to test the vacuum within a hermetically sealed package for a microelectronic and/or microelectromechanical device. As shown in FIG. 13, a hermetically sealed package can be defined by the substrate 301, the sidewalls 303 and 305, and the capping layer 307 to provide a sealed cavity 309. An acceleration mass 311 can be provided within this sealed cavity 309 along with associated microelectronic circuitry to provide an accelerometer, and a fixed pressure is preferable maintained within the sealed cavity.

More particularly, the acceleration mass 311 can be supported by beams 313 that allow the acceleration mass to move within the sealed cavity 309 in response to an acceleration of the package. This movement can be electronically measured using variations, for example, in capacitance and/or piezoresistance to determine the acceleration. It is desirable to maintain a fixed pressure in the sealed cavity so that damping of the acceleration mass remains relatively constant to provide, for example, critical damping of the acceleration mass.

The beam 315 and the electrode 317 can thus be used as discussed above, to measure the air pressure within the sealed cavity 309. In particular, an electric signal can be generated across the beam 315 and the electrode 317 so that the beam deflects toward the electrode. The interval of time between the generation of the signal and the full deflection of the beam is directly proportional to the air pressure within the sealed cavity. A measurement of the time interval can thus be used to determine if an acceptable fixed pressure has been maintained within the sealed cavity to provide adequate operation of the accelerometer. If the fixed pressure has been compromised, a signal can be generated indicating that the seal has failed.

The sidewalls 303 and 305 can be provided by patterned insulating layers such as patterned oxide and/or nitride layers. The acceleration mass 311 and the beams 313 can be provided simultaneously using wafer bonding techniques. The capping layer 307 can also be provided using wafer bonding techniques. Furthermore, fluid communication is provided through the sealed cavity 309 including portions 309a, 309b, and 309c around beams 313 and 315. While the pressure sensor of FIG. 13 is discussed including the beam 315, the pressure sensor can alternately include a plate or a diaphragm. Alternately, the fluid property sensor can be provided adjacent a microelectromechanical structure or a microelectronic circuit within the hermetically sealed cavity of a package such as a DIP package or a metal can package.

In the drawings and specification, there have been disclosed typical preferred embodiments of the invention and, although specific terms are employed, they are used in a generic and descriptive sense only and not for purposes of limitation, the scope of the invention being set forth in the following claims. For example, the sensor structures discussed above have been discussed as being used to provide pressure measurements for compressible gasses. Alternately, these sensor structures can be used to measure fluid viscosities.

Moreover, an embodiment of a fluid property sensor has been discussed wherein a flexible member is electrostatically actuated and a predetermined deflection of the flexible member is determined using contact detection. Other means of actuation and/or detection, however, are included within the scope of the present invention. For example, the flexible member can be actuated electromagnetically, piezoelectrically, or electrothermally. Furthermore, the deflection of the flexible member can be determined, for example, using optical position detection, magnetic proximity detection, detection based on variations in capacitance, detection based on tunneling current measurements, or detection based on piezoresistive measurements.

The invention claimed is:

1. A fluid property sensor comprising:
   a substrate including a first electrode;
   a flexible member adjacent said substrate and said first electrode wherein said flexible member includes a second electrode;
   a signal generator which generates a predetermined electrical signal across said first and second electrodes so that an electrostatic force is generated between said first and second electrodes and so that said flexible member deflects a predetermined distance wherein an interval of time between the generation of said predetermined electrical signal and the deflection of said flexible member is dependent on a property of a fluid adjacent said flexible member; and
   a measuring circuit which measures the interval of time between the generation of said predetermined electrical signal and the deflection of said flexible member to said predetermined distance and that determines the property of the fluid adjacent said flexible member based on said interval of time.

2. A fluid property sensor according to claim 1 wherein said measuring circuit determines a viscosity of said fluid adjacent said flexible member based on said interval of time between the generation of said predetermined electrical signal and the deflection of said flexible member to said predetermined distance.

3. A fluid property sensor according to claim 1 wherein said fluid comprises a compressible gas and wherein said measuring circuit determines an absolute pressure of said compressible gas adjacent said flexible member based on said interval of time between the generation of said predetermined electrical signal and the deflection of said flexible member to said predetermined distance.

4. A fluid property sensor according to claim 1 wherein said flexible member is spaced apart from said substrate and said first electrode when in a non-deflected state, and a wherein said signal generator generates the predetermined electrical signal so that an attractive electrostatic force is generated between said first and second electrodes so that said flexible member deflects toward said substrate.

5. A fluid property sensor according to claim 4 wherein said electrostatic force is sufficient to cause a large enough deflection that said flexible member deflects toward said substrate so that said first and second electrodes make electrical contact and wherein said interval of time is measured between the generation of said predetermined electrical signal and said electrical contact between said first and second electrodes.

6. A fluid property sensor according to claim 1 wherein said flexible member comprises a polysilicon member.

7. A fluid property sensor according to claim 1 wherein said flexible member comprises a beam supported at one end thereon.

8. A fluid property sensor according to claim 1 wherein said flexible member comprises a beam supported at both ends thereof.

9. A fluid property sensor according to claim 1 wherein said flexible member comprises a plate supported by at least one beam.

10. A fluid property sensor according to claim 9 wherein said plate is rectangular.

11. A fluid property sensor according to claim 1 wherein said flexible member comprises a diaphragm.

12. A fluid property sensor according to claim 11 wherein said diaphragm defines a cavity between said diaphragm and said first electrode and wherein said cavity is vented.

13. A fluid property sensor according to claim 12 wherein said cavity is vented through holes in said diaphragm.

14. A fluid property sensor according to claim 1 wherein said first electrode comprises a polysilicon layer on said substrate.

15. A fluid property sensor according to claim 1 further comprising:
   a package defining a hermetically sealed cavity surrounding said flexible member and said first electrode.

16. A fluid property sensor according to claim 15 further comprising:
   an electronic device in said sealed cavity.

17. A fluid property sensor according to claim 15 further comprising:
   a microelectromechanical structure in said sealed cavity.

18. A fluid property sensor according to claim 1 wherein at least an edge of said flexible member is free of support and wherein fluid communication around said edge of said flexible member is provided for the fluid adjacent said flexible member.

19. A fluid property sensor according to claim 1 wherein fluid communication through a hole in said flexible member is provided for the fluid adjacent said flexible member.

20. A method of measuring a property of a fluid, said method comprising the steps of:
   providing a substrate including a first electrode;
   providing a flexible member adjacent said substrate and said first electrode wherein said flexible member includes a second electrode and wherein the fluid is adjacent said flexible member;
   generating a predetermined electrical signal across said first and second electrodes so that an electrostatic force is generated between said first and second electrodes and so that said flexible member deflects a predetermined distance wherein an interval of time between the generation of said predetermined electrical signal and the deflection of said flexible member to said predetermined distance is dependent on a property of a fluid adjacent said flexible member;

measuring the interval of time between the generation of said predetermined electrical signal and the deflection of said flexible member to said predetermined distance; and determining the property of the fluid adjacent said flexible member based on said interval of time.

21. A method according to claim 20 wherein said determining step comprises determining a viscosity of said fluid adjacent said flexible member based on said interval of time between the generation of said predetermined electrical signal and the deflection of said flexible member to said predetermined s distance.

22. A method according to claim 20 wherein said fluid comprises a compressible gas and wherein said determining step comprises determining an absolute pressure of said compressible gas adjacent said flexible member based on said interval of time between the generation of said predetermined electrical signal and the deflection of said flexible member to said predetermined distance.

23. A method according to claim 20 wherein said flexible member is spaced apart from said substrate and said first electrode when in a non-deflected state, and a wherein said predetermined electrical signal generates an attractive electrostatic force between said first and second electrodes so that said flexible member deflects toward said substrate.

24. A method according to claim 23 wherein said flexible member deflects toward said substrate so that said first and second electrodes make electrical contact and wherein said interval of time is measured between the generation of said predetermined electrical signal and said electrical contact between said first and second electrodes.

25. A method according to claim 20 wherein said flexible member comprises a polysilicon member.

26. A method according to claim 20 wherein said flexible member comprises a beam supported at one end thereof.

27. A method according to claim 20 wherein said flexible member comprises a beam supported at both ends thereof.

28. A method according to claim 20 wherein said flexible member comprises a plate supported by at least one beam.

29. A method according to claim 28 wherein said plate is rectangular.

30. A method according to claim 20 wherein said flexible member comprises a diaphragm.

31. A method according to claim 30 wherein said diaphragm defines a cavity between said diaphragm and said first electrode and wherein said cavity is vented.

32. A method according to claim 31 wherein said cavity is vented through holes in said diaphragm.

33. A method according to claim 31 wherein said first electrode comprises a polysilicon layer on said substrate.

34. A method according to claim 20 wherein at least an edge of said flexible member is free of support and wherein fluid communication around said edge of said flexible member is provided for the fluid adjacent said flexible member.

35. A method according to claim 20 wherein fluid communication through a hole in said flexible member is provided for the fluid adjacent said flexible member.

36. A method of forming a fluid property sensor, said method comprising the steps of:

forming a substrate including a first electrode;

forming a flexible member adjacent said substrate and said first electrode wherein said flexible member includes a second electrode adjacent said first electrode;

providing a signal generator which generates a predetermined electrical signal across said first and second electrodes so that an electrostatic force is generated between said first and second electrodes and so that said flexible member deflects a predetermined distance wherein an interval of time between the generation of said predetermined electrical signal and the deflection of said flexible member to said predetermined distance is dependent on a property of a fluid adjacent said flexible member; and providing a measuring circuit which measures the interval of time between the generation of said predetermined electrical signal and the deflection of said flexible member to said predetermined distance, and which determines the property of the fluid adjacent said flexible member based on said interval of time.

37. A method according to claim 36 wherein said measuring circuit determines a viscosity of said fluid adjacent said flexible member based on said interval of time between the generation of the predetermined electrical signal and the deflection of said flexible member to said predetermined distance.

38. A method according to claim 36 wherein said fluid comprises a compressible gas and wherein said measuring circuit determines an absolute pressure of said compressible gas adjacent said flexible member based on said interval of time between the generation of said predetermined electrical signal and the deflection of said flexible member to said predetermined distance.

39. A method according to claim 36 wherein said flexible member is spaced apart from said substrate and said first electrode when in a non-deflected state, and a wherein said signal generator generates the predetermined electrical signal so that an attractive electrostatic force is generated between said first and second electrodes so that said flexible member deflects toward said substrate.

40. A method according to claim 39 wherein said flexible member deflects toward said substrate so that said first and second electrodes make electrical contact and wherein said interval of time is measured between the generation of said predetermined electrical signal and said electrical contact between said first and second electrodes.

41. A method according to claim 36 wherein said flexible member comprises a polysilicon member.

42. A method according to claim 36 wherein said flexible member comprises a beam supported at one end thereon.

43. A method according to claim 36 wherein said flexible member comprises a beam supported at both ends thereof.

44. A method according to claim 36 wherein said flexible member comprises a plate supported by at least one beam.

45. A method according to claim 44 wherein said plate is rectangular.

46. A method according to claim 36 wherein said flexible member comprises a diaphragm.

47. A method according to claim 46 wherein said diaphragm defines a cavity between said diaphragm and said first electrode and wherein said cavity is vented.

48. A method according to claim 47 wherein said cavity is vented through holes in said diaphragm.

49. A method according to claim 47 wherein said first electrode comprises a polysilicon layer on said substrate.

50. A method according to claim 36 wherein at least an edge of said flexible member is free of support and wherein fluid communication around said edge of said flexible member is provided for the fluid adjacent said flexible member.

51. A method according to claim 36 wherein fluid communication through a hole in said flexible member is provided for the fluid adjacent said flexible member.

52. A fluid property sensor comprising:

a flexible member adjacent a substrate;

generator means for generating a force so that said flexible member deflects a predetermined distance wherein an interval of time between the generation of said force and the deflection of said flexible member to said predetermined distance is dependent on a property of a fluid adjacent said flexible member; and a measuring means for measuring the interval of time between the generation of said force and the deflection of said flexible member to said predetermined distance and for determining the property of the fluid adjacent said flexible member based on said interval of time.

53. A fluid property sensor according to claim 52 wherein said measuring means determines a viscosity of said fluid adjacent said flexible member based on said interval of time between the generation of said force and the deflection of said flexible member to said predetermined distance.

54. A fluid property sensor according to claim 52 wherein said fluid comprises a compressible gas and wherein said measuring means determines an absolute pressure of said compressible gas adjacent said flexible member based on said interval of time between the generation of said force and the deflection of said flexible member to said predetermined distance.

55. A fluid property sensor according to claim 52 wherein said flexible member is spaced apart from said substrate when in a non-deflected state, and a wherein said flexible member deflects toward said substrate responsive to said force.

56. A fluid property sensor according to claim 55 wherein said flexible member deflects toward said substrate so that said flexible member and said substrate make contact and wherein said interval of time is measured between the generation of said force and said contact between said flexible member and said substrate.

57. A fluid property sensor according to claim 52 wherein said generator means generates one of an electrostatic force, an electromagnetic force, a piezoelectric force, and an electrothermal force.

58. A fluid property sensor according to claim 52 wherein said measuring means determines said deflection of said flexible member using one of tunneling current measurements, piezoresistive measurements, resonant strain gauge measurements, capacitance measurements, magnetic proximity measurements, and optical detection measurements.

59. A fluid property sensor according to claim 52 wherein at least an edge of said flexible member is free of support and wherein fluid communication around said edge of said flexible member is provided for the fluid adjacent said flexible member.

60. A fluid property sensor according to claim 52 wherein fluid communication through a hole in said flexible member is provided for the fluid adjacent said flexible member.

61. A method of measuring a property of a fluid using a sensor including a substrate and a flexible member adjacent the substrate, wherein the fluid is adjacent the flexible member, said method comprising the steps of:

applying a force to said flexible member so that said flexible member deflects a predetermined distance wherein an interval of time between the application of said force and the deflection of said flexible member to said predetermined distance is dependent on a property of a fluid adjacent said flexible member;

measuring the interval of time between the application of said force and the deflection of said flexible member to said predetermined distance; and determining the property of the fluid adjacent said flexible member based on said interval of time.

62. A method according to claim 61 wherein said determining step comprises determining a viscosity of said fluid adjacent said flexible member based on said interval of time between the generation of said force and the deflection of said flexible member to said predetermined distance.

63. A method according to claim 61 wherein said fluid comprises a compressible gas and wherein said determining step comprises determining an absolute pressure of said compressible gas adjacent said flexible member based on said interval of time between the generation of said force and the deflection of said flexible member to said predetermined distance.

64. A method according to claim 61 wherein said flexible member is spaced apart from said substrate when in a non-deflected state, and wherein said force generates an attractive force so that said flexible member deflects toward said substrate responsive to said force.

65. A method according to claim 64 wherein said flexible member deflects toward said substrate so that said flexible member and said substrate make contact and wherein said interval of time is measured between the generation of said force and said contact between flexible member and said substrate.

66. A method according to claim 61 wherein said step of generating said force comprises generating one of an electrostatic force, an electromagnetic force, a piezoelectric force, and an electrothermal force.

67. A method according to claim 61 wherein said deflection of said flexible member is determined using one of tunneling current measurements, piezoresistive measurements, resonant strain gauge measurements, capacitance measurements, magnetic proximity measurements, and optical detection measurements.

68. A method according to claim 61 wherein at least an edge of said flexible member is free of support and wherein fluid communication around said edge of said flexible member is provided for the fluid adjacent said flexible member.

69. A method according to claim 61 wherein fluid communication through a hole in said flexible member is provided for the fluid adjacent said flexible member.

70. A fluid property sensor comprising:

a flexible member adjacent a substrate;

an actuator which applies a predetermined force to said flexible member so that said flexible member deflects a predetermined distance wherein an interval of time between the application of said force to said flexible member and the deflection of said flexible member to said predetermined distance is dependent on a property of a fluid adjacent said flexible member; and a measuring circuit which measures the interval of time between the application of said force to said flexible member and the deflection of said flexible member to said predetermined distance and for determining the property of the fluid adjacent said flexible member based on said interval of time.

71. A fluid property sensor according to claim 70 wherein said measuring circuit determines a viscosity of said fluid adjacent said flexible member based on said interval of time between the application of said force and the deflection of said flexible member to said predetermined distance.

72. A fluid property sensor according to claim 70 wherein said fluid comprises a compressible gas and wherein said measuring circuit determines an absolute pressure of said compressible gas adjacent said flexible member based on said interval of time between the application of said force and the deflection of said flexible member to said predetermined distance.

74. A fluid property sensor according to claim 70 wherein said flexible member is spaced apart from said substrate when in a non-deflected state, and wherein said flexible member deflects toward said substrate responsive to said force.

74. A fluid property sensor according to claim 73 wherein said flexible member deflects toward said substrate so that said substrate and flexible member make contact and wherein said interval of time is measured between the application of said force and said contact between said flexible member and said substrate.

75. A fluid property sensor according to claim 70 wherein said actuator applies one of an electrostatic force, an electromagnetic force, a piezoelectric force, and an electrothermal force.

76. A fluid property sensor according to claim 70 wherein said measuring circuit determines said deflection of said flexible member using one of tunneling current measurements, piezoresistive measurements, resonant strain gauge measurements, capacitance measurements, magnetic proximity measurements, and optical detection measurements.

77. A fluid property sensor according to claim 70 wherein at least an edge of said flexible member is free of support and wherein fluid communication around said edge of said flexible member is provided for the fluid adjacent said flexible member.

78. A fluid property sensor according to claim 70 wherein fluid communication through a hole in said flexible member is provided for the fluid adjacent said flexible member.

* * * * *